United States Patent
Blanz et al.

(10) Patent No.: US 7,418,078 B2
(45) Date of Patent: Aug. 26, 2008

(54) SPOT-SIZE EFFECT REDUCTION

(75) Inventors: Wolf-Ekkehard Blanz, Danville, CA (US); Ali Bani-Hashemi, Walnut Creek, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 264 days.

(21) Appl. No.: 11/123,749

(22) Filed: May 6, 2005

(65) Prior Publication Data

US 2006/0251212 A1    Nov. 9, 2006

(51) Int. Cl.
*G01N 23/04* (2006.01)

(52) U.S. Cl. .............................. 378/62; 378/19; 378/65; 378/98.3

(58) Field of Classification Search .................... 378/4, 378/16, 19, 62, 901, 65, 98.3; 382/131, 260
See application file for complete search history.

(56) References Cited

U.S. PATENT DOCUMENTS

| | | | | |
|---|---|---|---|---|
| 4,497,062 A | * | 1/1985 | Mistretta et al. | 378/158 |
| 4,872,187 A | * | 10/1989 | Nakahata et al. | 378/4 |
| 5,235,191 A | * | 8/1993 | Miller | 378/98.3 |
| 5,757,951 A | * | 5/1998 | Tuy | 382/131 |
| 5,878,108 A | * | 3/1999 | Baba et al. | 378/98.4 |
| 6,031,892 A | * | 2/2000 | Karellas | 378/98.3 |

\* cited by examiner

*Primary Examiner*—Chih-Cheng G Kao

(57) ABSTRACT

A radiographic imaging device includes an X-ray source having a finite focal spot characterized by a determined intensity distribution. The X-ray source emits a beam of X-ray radiation toward an object. A detector assembly receives at least part of the X-ray radiation after it passes through the object. The detector assembly produces a signal in response to the received radiation. An image processor constructs an image from the signal generated by the detector assembly using the determined intensity distribution of the X-ray source. By inverse filtering the aggregated detector image from the detector assembly, the effects of the finite focal spot size of the X-ray source are mitigated, improving the quality of the resulting image.

16 Claims, 4 Drawing Sheets

SPOT-SIZE EFFECT REDUCTION

BACKGROUND OF THE INVENTION

The present invention relates generally to radiographic imaging devices, and more specifically to a system and method for mitigating the distortion effects of larger spot sizes thereby allowing the image quality of the radiographic imaging device to be improved. The present invention is particularly applicable to X-ray imaging technologies operating in the megavolt (MV) range, such as imaging technologies utilized in radiation therapy.

The quality of X-ray images produced by a radiographic imaging device is determined by a variety of factors. One factor is the size of the focal spot of the source that emanates the X-ray radiation. X-ray tubes for diagnostic applications operating somewhere between 80 kV and 120 kV of incident electron energies have made substantial progress over the years, attaining spot-sizes of much less than 1 mm, which in turn leads to good image quality in diagnostic X-ray imaging.

With the introduction of imaging technologies in radiation therapy, X-ray imaging in the megavolt range, with photon energies between 6 MV and 24 MV, is of significant interest. Linear accelerators for radiation therapy, however, were initially not designed as imaging devices, and hence no substantial engineering efforts have been expended to reduce the spot size of those accelerators to spot sizes provided by conventional X-ray tubes. When a linear accelerator is used as the X-ray source for imaging, it is more difficult to control the electrons to a very small spot size. In radiation therapy, where high dose rates are needed, larger spot sizes may be more desirable from an engineering point of view, since spot sizes which are too small might overheat the target locally.

For these reasons, spot sizes in megavolt (MV) imaging are considerably larger than spot sizes in kilovolt (kV) diagnostic imaging and have diameters significantly larger than 1 mm. The effect of these larger spot sizes is an inherent blurring of the images generated by the radiographic imaging device. Since reducing the spot size of medical linear accelerators below a certain size may not be practical or desirable, it would be desirable to develop apparatus and methods for reducing or mitigating the effects of larger spot sizes rather than reducing the spot size itself.

SUMMARY OF THE INVENTION

Accordingly, the present invention is directed to apparatus and methods for mitigating the adverse effects of finite spot sizes on image quality, thereby allowing the image quality of the radiographic imaging device to be improved.

In one embodiment, a radiographic imaging device includes an X-ray source having a finite focal spot characterized by a determined intensity distribution. By first measuring the intensity distribution for the X-ray source, the intensity distribution may subsequently be utilized for improving the image quality of the radiographic imaging device. For instance, the X-ray source may emit a beam of X-ray radiation toward an object. A detector assembly receives at least part of the X-ray radiation after it passes through the object and produces a signal in response to the received radiation. An image processor may then construct an image from the signal generated by the detector using the determined intensity distribution of the X-ray source.

Without loss of generality, we can assume that an object consists of a number of planar layers. To generate an X-ray image, each layer of the object undergoes an X-ray projection onto the detector. An aggregate of these projections then forms the X-ray image of the object.

By utilizing the determined intensity distribution of the X-ray source and inverse filtering the aggregated detector image d(x) from the detector assembly with this intensity distribution scaled for one particular layer of the object, the distortion effects of the finite focal spot size of the X-ray source are mitigated for this layer, allowing novel uses of the resulting aggregated image and ultimately leading to an improved diagnostic value of the measured data. For example, in one embodiment, the measured detector signal d(x) is convolved with an inverse filter $g_{h1}^{-1}(x)$ in the image domain, while in another embodiment, the Fourier transform of d(x), D(u), is multiplied by the inverse of the Fourier transform of $g_{h1}(x)$, $1/G_{h1}(u)$, in the Fourier domain. In this manner, the contribution of one particular layer to the overall projection image is sharpened.

It is to be understood that both the foregoing general description and the following detailed description are exemplary and explanatory only and are not necessarily restrictive of the invention as claimed. The accompanying drawings, which are incorporated in and constitute a part of the specification, illustrate an embodiment of the invention and together with the general description, serve to explain the principles of the invention.

DETAILED DESCRIPTION OF SPECIFIC EMBODIMENTS

Reference will now be made in detail to the presently preferred embodiments of the invention, examples of which are illustrated in the accompanying drawings.

Figure 1:
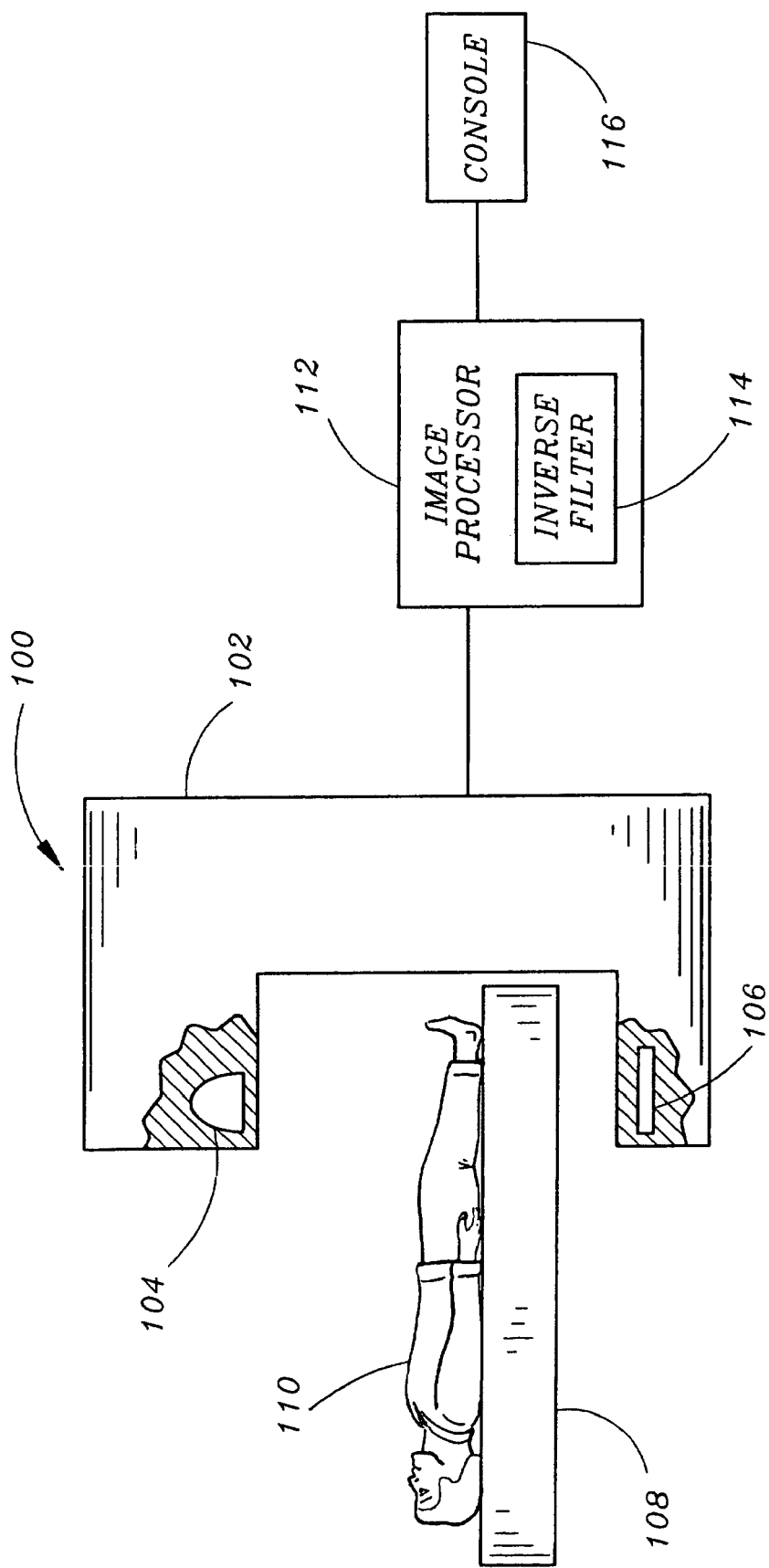
FIG. 1 is a diagrammatic view illustrating a radiographic imaging device in accordance with an exemplary embodiment of the present invention.

FIG. 1 illustrates a radiographic imaging device in accordance with an exemplary embodiment of the present invention. The radiographic imaging device 100 includes a scanning unit or gantry 102 supporting an X-ray source 104 and a detector assembly 106, and a patient table 108 for supporting a patient 110 undergoing radiographic imaging. For example, the radiographic imaging device 100 may be a cone beam computed tomography (CBCT) imaging device operating in the megavolt range. The detector assembly 106 includes a plurality of detection elements (e.g., ultra fast ceramic (UFC) detectors, amorphous silicon flat panel detectors, charged coupled device (CCD) detectors, or the like) which convert incident X-rays of varying intensity to analog electrical signals. These analog signals are then amplified and converted to digital signals which are processed by an image processor 112 to produce an image comprising a plurality of pixels, each representing the intensity of measured X-ray radiation incident on a detection element of the detector assembly 106.

The image processor 112 utilizes an inverse filter 114 derived from a measured intensity distribution of the X-ray source 104. A console 116 provides a man-machine interface with the imaging device 100. For example, the console 116 may function as the control unit for controlling the imaging device 100 during examination procedures. The console 116 may further be used by physicians or technicians for evaluating the examination results.

For the following discussion, the notation has been simplified by restricting the exemplary embodiments to a two-dimensional case. Those of skill in the art will appreciate that the extension to three dimensions is straightforward and does not provide additional problems or insights.

Figure 2:
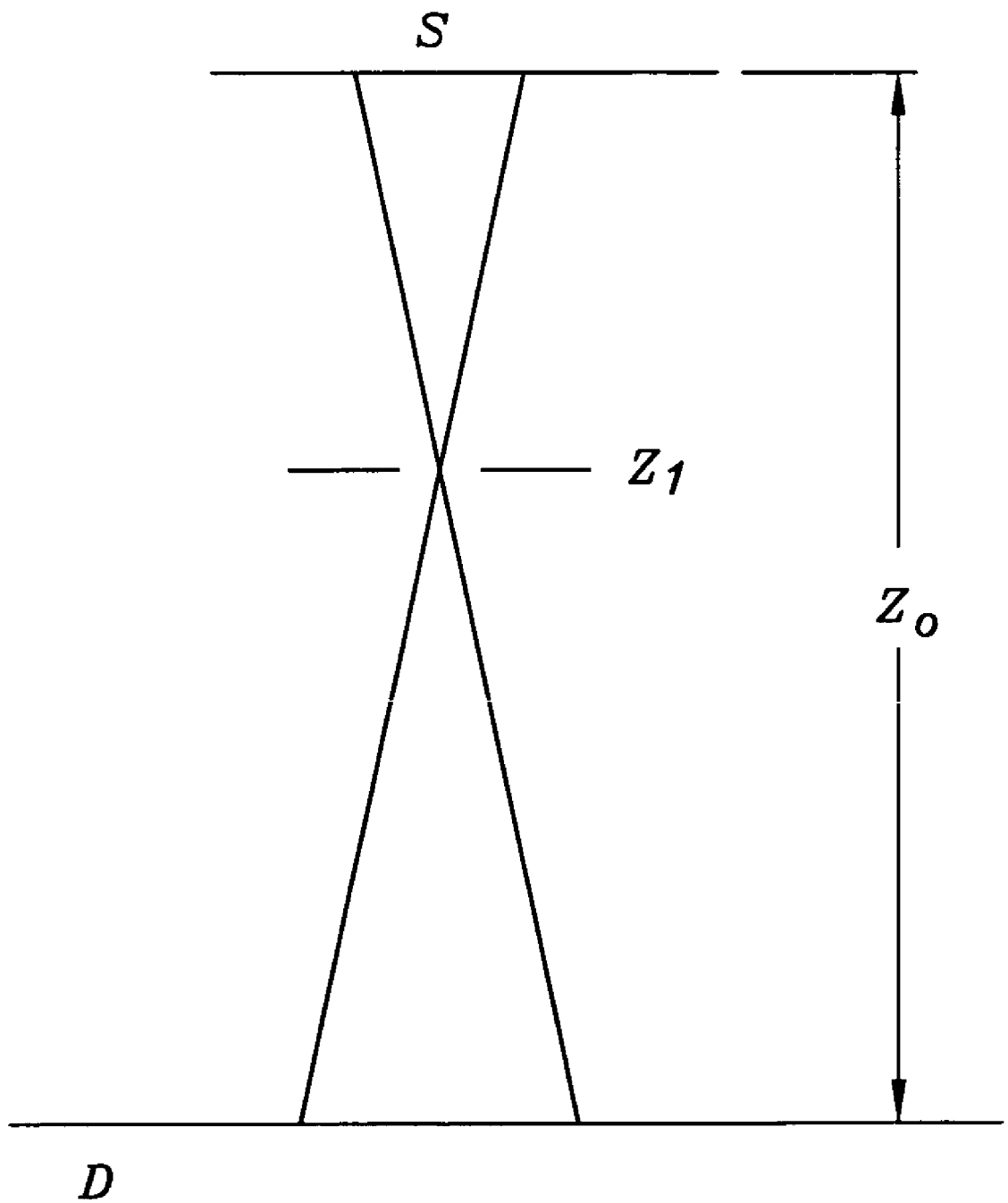
FIG. 2 is a diagrammatic illustration of radiographic cone beam imaging geometry for measuring the Point Spread Function (PSF) of an optical system.

FIG. 2 illustrates radiographic imaging geometry, including a radiation source, a pinhole at a particular object layer $z_1$, and a detector at a distance $z_0$ from the radiation source. Those of skill in the art will appreciate that FIG. 2 depicts a geometry for measuring the Point Spread Function (PSF) of an optical system and that the image measured at the detector is mathematically described as the scaled image at the object layer $z_1$ convolved with the PSF. Simple geometric considerations employing the intercept theorem lead to a scale factor of $$\frac{z_0 - z_1}{z_1}$$

for converting the intensity distribution at the focal spot to the PSF, and a factor of $$\frac{z_0}{z_1}$$

for the projection of an object at layer $z_1$ onto the detector. We also note that while the image of the object layer at $z_1$ has the same orientation as the object layer, the PSF is a mirror image of the intensity distribution at the focal spot. The image that the detector sees of an object layer is mathematically described as $$i(x) = o\left(x \cdot \frac{z_1}{z_0}, z_1\right) * s\left(-x \cdot \frac{z_1}{z_0 - z_1}\right)$$

where the symbol * denotes the convolution operation.

When we now move from a single layer object at $z_1$ to an object that extends over a finite size from $z_{top}$ to $z_{bottom}$, the aggregate image at the detector becomes $$i(x) = \int_{z_1 = z_{top}}^{z_{bottom}} o\left(x \cdot \frac{z_1}{z_0}, z_1\right) * s\left(-x \cdot \frac{z_1}{z_0 - z_1}\right) dz_1$$

In other words, the aggregate image at the detector is composed of the images of all the individual layers of the object, each magnified by a slightly different factor $$\frac{z_0}{z_1}$$

and each convolved with its own PSF, which is scaled differently for each layer, depending on the layer's distance to the source $z_1$.

Because each layer has been blurred with a differently scaled PSF, it is possible to deblur the aggregate detector signal for the contribution of one particular layer, for each layer at a time. Several techniques to deblur images for known PSFs may be utilized with the present invention, such as inverse filtering, Wiener filtering, the Tikhonov-Miller restoration, the SECB method, and many iterative procedures such as the Lucy-Richardson procedure. However, those of skill in the art will appreciate that the present invention is not limited to any particular method for deblurring.

In one embodiment, the so enhanced aggregate detector signal is utilized for generating a "flip-book"-type presentation of the detector image. For example, the user is presented a changing series of images (e.g. a video) where the contribution of each layer of the volume is sharpened to produce a corresponding frame of the video. For instance, the detector image may be sharpened utilizing a scaled PSF for each layer, starting from object layer $z_{top}$ and extending to object layer $z_{bottom}$ or, alternatively, starting from object layer $z_{bottom}$ and extending to object layer $z_{top}$. Alternatively, the user may specify a scaled PSF for a desired layer to sharpen the detector image. Those of skill in the art will appreciate that a detector image sharpened utilizing the apparatus and method of the present invention may be presented in a variety of ways without departing from the scope and spirit thereof.

In another embodiment, a maximum sharpness projection may be generated utilizing the enhanced aggregate detector signal. For instance, analogously to a Maximum Intensity Projection (MIP), the detector image may be apportioned (e.g. divided into a grid), and for each portion of the grid a corresponding portion of a sharpened detector image is selected. For example, a portion of the detector image having the highest local frequency content, is selected for each portion of the grid from the set of detector images sharpened utilizing the scaled PSF for each layer of the aggregate detector signal. The various portions selected from the set of sharpened detector images are then combined, and the resulting image is displayed in a single viewing plane.

In a further embodiment, cone beam or CT reconstruction with sharpened layers is provided. For example, when reconstructing a particular three-dimensional pixel, or voxel, for a given aggregate detector signal representing the volume of an object being scanned by the cone beam or CT scanner, the raw data is sharpened for the object layer of that particular voxel utilizing the PSF for that layer.

Figure 3:
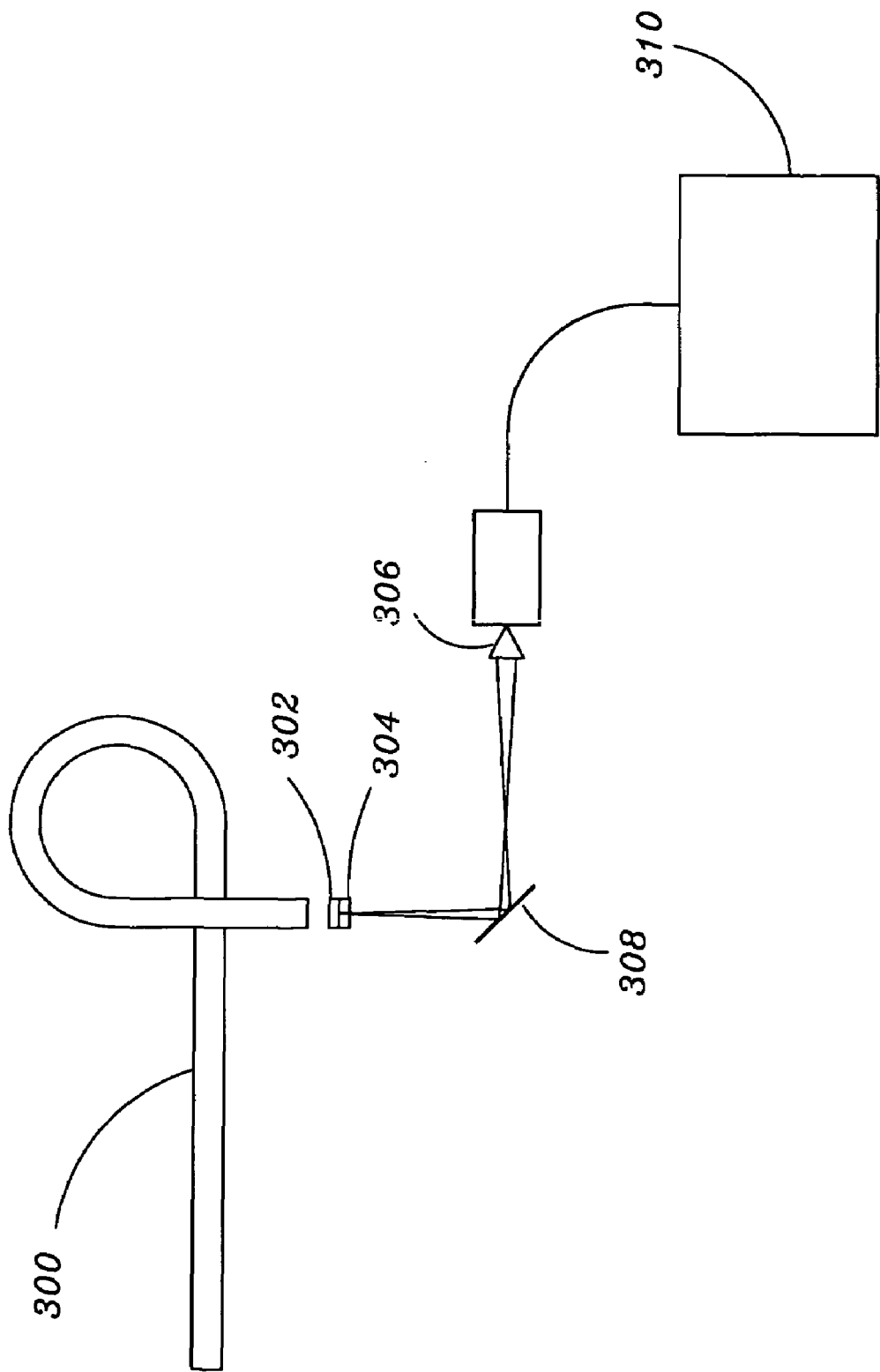
FIG. 3 is a diagrammatic view illustrating apparatus for measuring the intensity profile of a radiographic source in accordance with an exemplary embodiment of the present invention.

Referring FIG. 3, in order to inverse filter the measured detector signal with the PSF, i.e. the mirrored intensity distribution of the X-ray source, the intensity distribution is first measured. The size of the focal spot of a linear accelerator can be relatively easily measured using an imaging device such as a camera or the like, which detects light from scintillation material onto which the X-ray beam is directed. For example, F*i*G. 3 depicts a geometry wherein X-ray radiation emanating from a waveguide 300 is directed toward a target 302. A scintillation screen 304 is placed directly at the target 302 of the waveguide 300 so as not to incur unnecessary geometric distortion of the measured spot intensity profile. An imaging device such as a camera 306 then detects the light emitted from the scintillation screen 304. To protect the camera 306 from direct X-ray radiation, a mirror 308 is brought into the optical path for directing light from the scintillation screen 304 to the imaging device or camera 306. In one embodiment, the mirror 308 is positioned at an angle of forty-five degrees (45°) with respect to the camera 306 and the scintillation screen 304 for directing the light at an angle suitable for the chosen geometry with respect to the center beam line. Those of skill in the art will appreciate that other angles may be selected for positioning the mirror 308 depending on the geometry of the waveguide 300, the target 302, and the like. The camera 306, which is oriented toward the mirror 308, produces an image signal containing the intensity distribution. A digitizer (e.g., within the camera 306) converts the image signal into a computer-readable matrix of pixel information, which may then be analyzed by a computer 310, or the like, for measuring the intensity distribution of the X-ray source.

Irrespective of the particular geometry and even if the profile should not be exactly Gaussian, the true and geometrically corrected intensity profile is represented in the resulting images. These profiles can then be stored for each linear accelerator tube individually. The PSF will then be obtained as previously described. The images generated by these accelerators can be reconstructed with the machine-specific intensity profiles.

Figure 4:
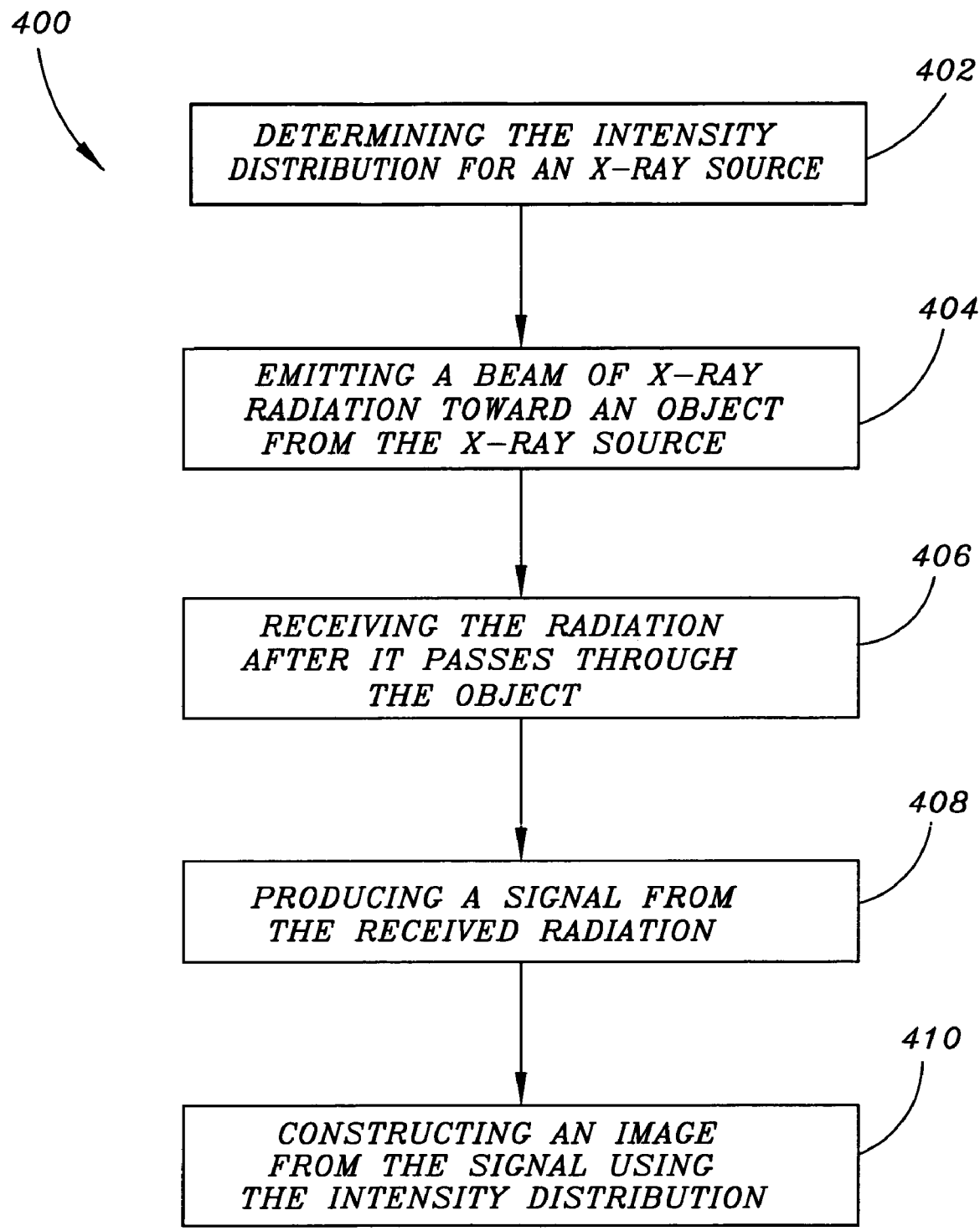
FIG. 4 is a flow diagram illustrating a method for mitigating the distortion effects of finite spot size on a radiographic image in accordance with an exemplary embodiment of the present invention.

Referring now to FIG. 4, a method 400 for utilizing the determined intensity distribution and inverse filtering the aggregated detector image d(x) from a detector assembly is described. Accordingly, a radiographic imaging device includes an X-ray source having a finite focal spot characterized by a determined intensity distribution. By first measuring the intensity distribution for the X-ray source 402, the intensity distribution is subsequently utilized for generating detector signals with enhanced individual layer contributions. For instance, the X-ray source emits a beam of X-ray radiation toward an object 404. Then, a detector assembly receives at least part of the X-ray radiation after it passes through the object 406. The detector assembly produces a signal in response to the received radiation 408. Next, an image processor constructs an image from the signal generated by the detector using the determined intensity distribution of the X-ray source 410.

In the exemplary embodiments, method 400 may be implemented as sets of instructions or software readable by the radiographic imaging device. Further, it is understood that the specific order or hierarchy of steps in the methods disclosed are examples of exemplary approaches. Based upon design preferences, it is understood that the specific order or hierarchy of steps in the method can be rearranged while remaining within the scope and spirit of the present invention. The accompanying method claims present elements of the various steps in a sample order, and are not necessarily meant to be limited to the specific order or hierarchy presented.

It is believed that the present invention and many of its attendant advantages will be understood by the foregoing description, and it will be apparent that various changes may be made in the form, construction and arrangement of the components thereof without departing from the scope and spirit of the invention or without sacrificing all of its material advantages. The form herein before described being merely an explanatory embodiment thereof, it is the intention of the following claims to encompass and include such changes.

What is claimed is:

1. A radiographic imaging device, comprising:
   an X-ray source for emitting a beam of X-ray radiation toward an object, the X-ray source having a finite focal spot characterized by an X-ray intensity distribution;
   a detector assembly for receiving at least part of the X-ray radiation after the X-ray radiation passes through the object and producing a signal in response thereto; and
   an image processor configured to construct an image from the signal generated by the detector,
   wherein the image processor constructs the image by: scaling the intensity distribution for a first object layer; scaling the intensity distribution for a second object layer; aggregating the first and second scaled intensity distributions; and applying a filter to the aggregated scaled intensity distributions.

2. The radiographic imaging device as claimed in claim 1, wherein the application of the filter is a convolution of the aggregated scaled intensity distributions and an inverse filter derived from the X-ray intensity distribution.

3. The radiographic imaging device as claimed in claim 1, wherein the application of the filter comprises: multiplication of a Fourier transform of the aggregated scaled intensity distributions with an inverse of a Fourier transform of an inverse filter derived from the X-ray intensity distribution; and
   computation of a transform of the product of the multiplication from the Fourier domain to an image domain.

4. The radiographic imaging device as claimed in claim 1, wherein the object comprises a plurality of layers, and the image is constructed by filtering utilizing a scaled point spread function (PSF) determined for a specified object layer of the plurality of layers, the image being for at least one of a video presentation, a maximum sharpness projection of the object, and reconstruction of a voxel associated with the specified object layer.

5. The radiographic imaging device as claimed in claim 1, further comprising an apparatus for determining the X-ray intensity distribution of the X-ray source, including:
   a scintillation screen placed within the beam of the X-ray radiation, the beam of X-ray radiation causing the scintillation screen to emit light having an intensity distribution corresponding to the intensity distribution of the finite focal spot;
   an imaging device for detecting the light emitted by the scintillation screen and producing an image signal in response thereto, the image signal containing the intensity distribution; and
   a digitizer for converting the image signal into a computer-readable matrix of pixel information,
   wherein the scintillation screen is positioned substantially adjacent to the object.

6. The radiographic imaging device as claimed in claim 5, wherein the apparatus further comprises a mirror for directing light from the scintillation screen to the imaging device.

7. The radiographic imaging device as claimed in claim 6, wherein the mirror is positioned at an angle of forty-five degrees (45°) with respect to the imaging device and the scintillation screen.

8. The radiographic imaging device as claimed in claim 6, wherein the imaging device comprises a camera.

9. A method for mitigating the effect of finite focal spot size in a radiographic imaging device, the radiographic imaging device having an X-ray source having a finite focal spot for emitting X-ray radiation toward an object so that at least part of the X-ray radiation passes through the object, comprising:
   determining an intensity distribution for the X-ray source;
   receiving at least part of a beam of X-ray radiation emitted by the X-ray source after the beam of X-ray radiation passes through the object and producing a signal in response thereto;
   constructing an image from the signal generated by the detector by:
   scaling the intensity distribution for a first object layer;
   scaling the intensity distribution for a second object layer;
   aggregating the first and second scaled intensity distributions; and filtering the aggregated scaled intensity distributions, and
displaying the image on a display console.

10. The method as claimed in claim 9, wherein the filtering comprises: computing a convolution of the aggregated scaled intensity distributions and an inverse filter derived from the X-ray intensity distribution.

11. The method as claimed in claim 9, wherein the filtering comprises: multiplying a Fourier transform of the aggregated scaled intensity distributions and an inverse of a Fourier transform of an inverse filter derived from the X-ray intensity distribution; and
  computing a transform of the product of the multiplication from the Fourier domain to an image domain.

12. The method as claimed in claim 9, wherein the object comprises a plurality of layers, and the image is constructed by filtering utilizing a scaled point spread function (PSF) determined for a specified object layer of the plurality of layers, the image being for at least one of a video presentation, a maximum sharpness projection of the object, and reconstruction of a voxel associated with the specified object layer.

13. The method as claimed in claim 9, wherein determining the intensity distribution for the X-ray source comprises:

passing the beam of X-ray radiation through a scintillation screen, the beam of X-ray radiation causing the scintillation screen to emit light having an intensity distribution corresponding to the intensity distribution of the finite focal spot;

detecting the light emitted by the scintillation screen and producing an image signal in response thereto, the image signal containing the intensity distribution; and converting the image signal into a computer-readable matrix of pixel information, wherein the scintillation screen is positioned substantially adjacent to the object.

14. The radiographic imaging device as claimed in claim 13, further comprising directing light from the scintillation screen to the imaging device so that the imaging device is not within the beam of X-ray radiation.

15. The method as claimed in claim 14, wherein the step of directing the light comprises reflecting the light with a mirror positioned at an angle of forty-five degrees (45°) with respect to the imaging device and the scintillation screen.

16. The method as claimed in claim 14, wherein the imaging device comprises a camera.

* * * * *